(12) United States Patent
Rosen

(10) Patent No.: US 6,578,770 B1
(45) Date of Patent: Jun. 17, 2003

(54) THERMOSTAT INCORPORATING A CARBON DIOXIDE SENSOR SUITABLE FOR READING USING POTENTIOSTAT TECHNIQUES, AND ENVIRONMENTAL CONTROL SYSTEM INCORPORATING SUCH THERMOSTAT

(76) Inventor: Howard B. Rosen, 1 Lyncroft Road, Hampstead QC (CA), H3X 3E3

( * ) Notice: Subject to any disclaimer, the term of this patent is extended or adjusted under 35 U.S.C. 154(b) by 0 days.

(21) Appl. No.: 10/119,180

(22) Filed: Apr. 9, 2002

(51) Int. Cl.[7] .................................................. F24F 7/00
(52) U.S. Cl. ....................... 236/49.3; 73/31.05; 165/249
(58) Field of Search ................... 236/49.3, 11; 73/31.05; 165/248, 249; 454/256, 257, 258, 259, 239

(56) References Cited

U.S. PATENT DOCUMENTS

| | | | | |
|---|---|---|---|---|
| 4,326,200 A | * | 4/1982 | Bushman | 340/632 |
| 5,395,042 A | * | 3/1995 | Riley et al. | 236/46 R |
| 5,429,727 A | | 7/1995 | Vogt et al. | |
| 5,464,369 A | * | 11/1995 | Federspiel | 454/256 |
| 5,597,354 A | * | 1/1997 | Janu et al. | 454/229 |
| 5,772,863 A | | 6/1998 | Shoemaker et al. | |
| 5,775,406 A | * | 7/1998 | Ghitea, Jr. | 165/11.1 |
| 5,881,806 A | * | 3/1999 | Rudd | 165/244 |
| 5,971,067 A | * | 10/1999 | Rayburn et al. | 165/217 |
| 6,398,118 B1 | * | 6/2002 | Rosen et al. | 236/49.3 |
| 6,431,268 B1 | * | 8/2002 | Rudd | 165/223 |

* cited by examiner

*Primary Examiner*—Denise L. Esquivel
*Assistant Examiner*—Marc Norman

(57) ABSTRACT

A system for monitoring and modifying the quality and temperature of air within a conditioned space includes a blower unit, an optional damper unit for selectively admitting outside air into the conditioned space, a temperature moderating unit and a control unit. The control unit includes a thermostat and conventional temperature control apparatus for selectively activating the temperature moderating unit to maintain the desired temperature in the conditioned space. The control unit also incorporates $CO_2$ concentration measuring and control apparatus which employs a small $CO_2$ sensor. The $CO_2$ sensor includes upper and lower electrodes with an intermediate solid electrolyte. A voltage having a cyclic waveform is applied across the upper and lower electrodes, and the current through the $CO_2$ sensor is read at at least one predetermined voltage representing a $CO_2$ peak. The measured current is representative of the $CO_2$ concentration. $CO_2$ concentration modifying apparatus is responsive to sensing a first predetermined $CO_2$ concentration for turning on the blower unit and, optionally, to sensing a second, higher, predetermined $CO_2$ concentration for actuating the damper unit to admit outside air.

9 Claims, 5 Drawing Sheets

THERMOSTAT INCORPORATING A CARBON DIOXIDE SENSOR SUITABLE FOR READING USING POTENTIOSTAT TECHNIQUES, AND ENVIRONMENTAL CONTROL SYSTEM INCORPORATING SUCH THERMOSTAT

FIELD OF THE INVENTION

This invention relates to the art of conditioning indoor living, working and other enclosed public spaces. More particularly, this invention relates to a system in which the carbon dioxide ($CO_2$) level is monitored and controlled by apparatus in which the $CO_2$ sensor and support circuitry is integral with a thermostat which also serves to conventionally control the temperature range within the conditioned space.

BACKGROUND OF THE INVENTION

The ever increasing cost of energy has resulted, in recent years, in the construction of homes and buildings which are very well insulated and, further, which carefully provide for keeping the air within the home or building well isolated from the encroachment of outdoor air. This latter feature serves to limit the adverse effect of outdoor air on the desired temperature intended to be maintained within the building occasioned by direct mixing with the indoor air, an effect which is in addition to and independent of the limitation of adverse conduction effects afforded by insulating the conditioned spaces.

However, it has been observed that these highly-efficient, substantially closed, environmental conditioning systems have a serious drawback which can even reach dangerous levels. Because of the natural breathing processes of the occupants of a closed conditioned space and, in some instances, because of the effects of combustion or similar processes, the concentration level of oxygen ($O_2$) decreases while the concentration of carbon dioxide ($CO_2$) increases. It has been found that when the concentration of $CO_2$ in a conditioned space reaches on the order of 1000 parts per million (0.1%), breathing becomes noticeably more labored and difficult, particularly for those with breathing problems. Higher concentrations exacerbate these problems and can reach dangerous levels.

Accordingly, recommended maximum allowable concentrations of $CO_2$ for living and working spaces have been formulated and promulgated, and, in some instances, various government agencies have imposed requirements that specify the maximum concentration of $CO_2$ which will be allowed in public conditioned spaces.

Commercial $CO_2$ detectors have been not only bulky, but have also provided measurements of $CO_2$ concentration only across a very narrow, low level range. One commonly used $CO_2$ sensor in $CO_2$ detectors constitutes an IR light source directed at an IR light sensor such that the $CO_2$ concentration between the source and sensor subtly affects the response of the source. As a result, the support circuitry has to be able to interpret a suitably compensated signal (for example, for temperature and/or humidity variations) which may change only by a few microvolts across the entire measurement range.

A prior art approach to solving these problems is disclosed and claimed in U.S. patent application Ser. No. 09/240,506, filed Jan. 29, 1999, by Howard B. Rosen and Steven D. Dushane for Thermostat Incorporating Thin Film Carbon Dioxide Sensor and Environmental Control System, now U.S. Pat. No. 6,398,118, dated Jun. 4, 2002. In this reference, the $CO_2$ sensor consists of a cathode disposed on a substrate, an anode disposed on the substrate spaced from the cathode and a solid electrolyte disposed on the substrate intermediate and electrically in contact with each of the cathode electrode and the anode to effect a primary electrical cell. A heater and a heater thermostat are also disposed on the substrate and are connected to a source of electrical energy to maintain the primary electrical cell within a predetermined temperature on the order of 250° C. The metals from which the cathode and anode are fabricated and the chemical composition of the electrolyte were selected, as discussed in detail in the reference, such that the voltage established between the cathode and the anode varies in accordance with the $CO_2$ concentration at the primary electrical cell when the temperature of the cell is within the predetermined temperature range.

It has been found that the $CO_2$ sensor discussed in the above-identified reference has certain practical drawbacks when incorporated into a commercial thermostat. One significant practical problem is associated with the need to maintain the cell within the relatively high predetermined temperature range for both the short term (power consumption and heat stress on associated circuitry, particularly in a single chip embodiment) and the long term (operational life and creeping deterioration). Additional practical drawbacks include the relatively high cost of fabrication, limited robustness and generally limited long term reliability.

It is to overcoming these drawbacks of known space conditioning control systems which incorporate a $CO_2$ concentration control feature that the present invention is directed.

OBJECTS OF THE INVENTION

It is therefore a broad object of this invention to provide an improved $CO_2$ detector which is sufficiently compact and simple as to be suitable for integration with a thermostat in a single housing.

It is a more specific object of this invention, in a presently preferred embodiment, to incorporate into a thermostat a small, inexpensive and accurate $CO_2$ sensor which, if a heater is used, requires significantly less power to heat than the $CO_2$ sensor disclosed and claimed in the above identified reference and is more reliable in both the long and short terms.

SUMMARY OF THE INVENTION

Briefly, these and other features of the invention are found in a system for monitoring and modifying the quality and temperature of air within a conditioned space, which system includes a blower unit, an optional damper unit for selectively admitting outside air into the conditioned space, a temperature moderating unit and a control unit. The control unit includes a thermostat and conventional temperature control apparatus for selectively activating the temperature moderating unit to maintain the desired temperature in the conditioned space. The control unit also incorporates $CO_2$ concentration measuring and control apparatus which employees a small $CO_2$ sensor. The $CO_2$ sensor includes upper and lower electrodes with an intermediate solid electrolyte. A voltage having a cyclic waveform is applied across the upper and lower electrodes, and the current through the $CO_2$ sensor is read at at least one predetermined voltage representing a $CO_2$ peak. The measured current at the predetermined voltage is representative of the $CO_2$ concentration. $CO_2$ concentration modifying apparatus is responsive to sensing a first predetermined $CO_2$ concentration for turning on the blower unit and, optionally, to sensing a second, higher, predetermined $CO_2$ concentration for actuating the damper unit to admit outside air.

DESCRIPTION OF THE DRAWING

The subject matter of the invention is particularly pointed out and distinctly claimed in the concluding portion of the specification. The invention, however, both as to organization and method of operation, may best be understood by reference to the following description taken in conjunction with the subjoined claims and the accompanying drawing of which:

DESCRIPTION OF THE PREFERRED EMBODIMENT

Figure 1:
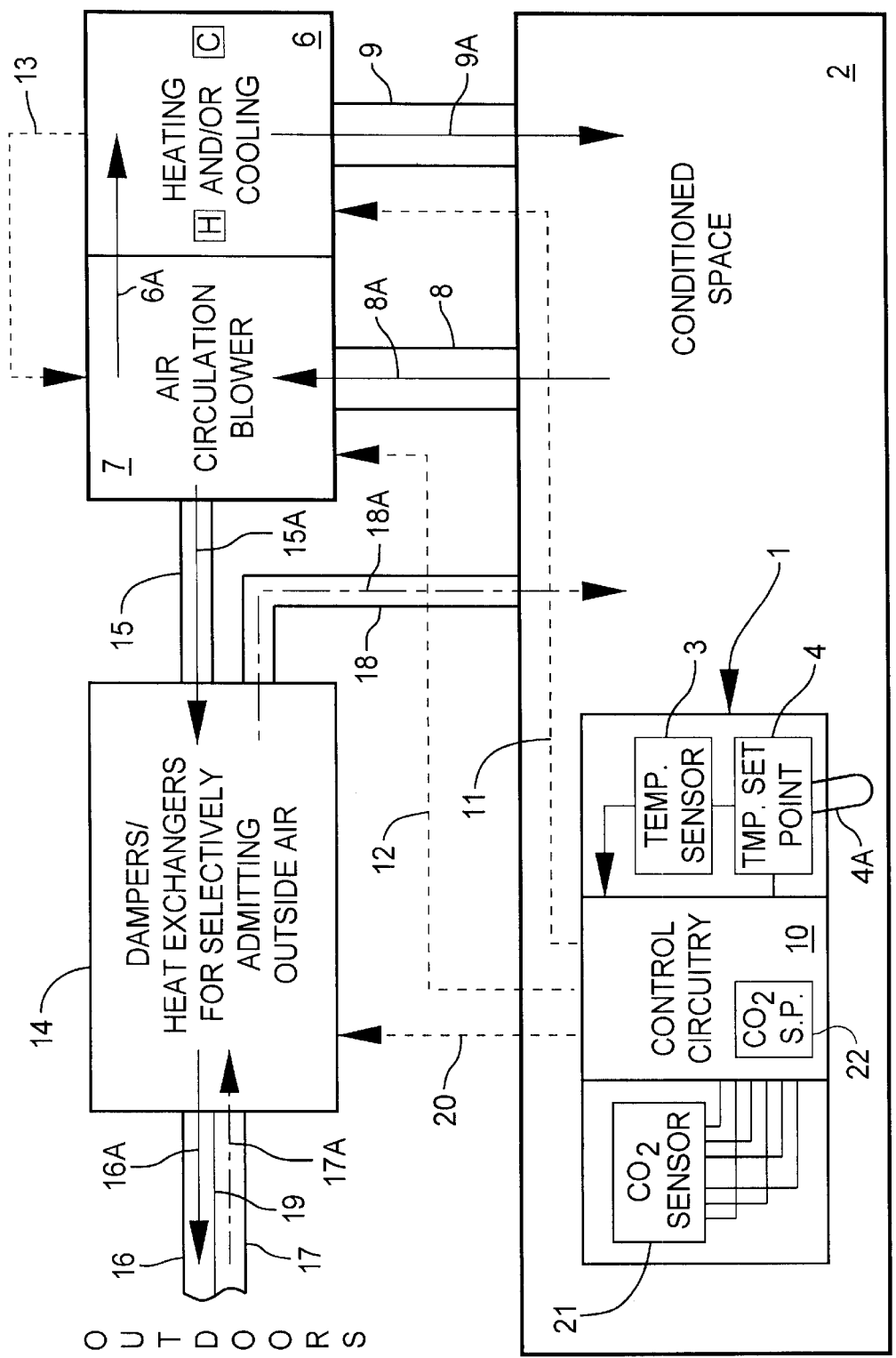
FIG. 1 is a high level block diagram illustrating an environment in which the present invention finds application.

Referring first to FIG. 1, an integrated thermostat/$CO_2$ level detector unit 1 is disposed within a conditioned space 2. The integrated unit 1 encloses a conventional temperature sensor 3, an adjustable set point device 4 and control circuitry 5 which issues suitable control signals to heating and/or cooling unit 6 (generically, a temperature moderating unit) and blower unit 7. Blower unit 7 serves to: withdraw air from the conditioned space via conduit(s) 8 (represented by the arrow 8A), selectively force the air taken in through the heating and/or cooling unit 6 (represented by the arrow 6A) and back to the conditioned space 2 via conduit(s) 9 (represented by the arrow 9A).

Conventionally, control circuitry 10 reads the set point 4, typically established by manually adjusting movable element 4A, and the temperature in the conditioned space 2 is sensed by the sensor 3 in a manner which can be interpreted by the control circuitry 10 as representing a temperature which can be compared to the current set point. (Those skilled in the art will understand that most modem thermostats employ "up" and "down" buttons and a digital readout in place of the manually adjusting movable element 4A which is merely a generic representation of any suitable apparatus for effecting manual control of the desired temperature.) Control circuitry 10 issues control signals to the heating and/or cooling unit 6 and to the blower unit 7 via conductors 11 and 12, respectively in the well known manner. For example, if the system is operating in the heating mode, when the control circuit 10 reads the temperature sensor 3 as indicating that the temperature in the conditioned space has dropped below the established set point (or some predetermined offset therefrom), it sends a signal on the line 11 to the heating components H of the heating and/or cooling unit 6 which institutes the heating process. Typically, after the heating process has been on for a few seconds, the heating and/or cooling unit sends a signal, via line 13, to the blower unit 7 to start air circulation through the conditioning system to thereby transfer heat from the heating components H to the conditioned space 2. When the temperature sensor 3 indicates that the conditioned space has been sufficiently heated (typically, to one or two degrees F. above the set point), the control circuitry 10 directs the heating process in the heating and/or cooling unit 6 to cease. Usually, the blower unit is allowed to continue to operate for a short period in order to extract the latent heat from the heating components H in the heating and/or cooling unit 6. In most heating and cooling systems, there is an option to independently manually control the blower unit 7 to run continuously or according to or taking into account some criteria other than the temperature of the working elements of the heating and/or cooling unit 6.

If the system is in the cooling mode, the system operates in a similar manner with the control circuitry 10 reading the temperature sensor 3 against the set point 4 and activating the cooling components C when the temperature in the conditioned space exceeds the set point (or some predetermined offset therefrom). Typically, air circulation is continued for a short period after the predetermined lower temperature of the conditioned space 2 has been reached in order to transfer additional heat to the cooling components C in the heating and/or cooling unit 6.

Those skilled in the art will appreciate that the temperature conditioning system for the conditioned space 2 so far described is entirely conventional and may be implemented in diverse variants (usually with more sophisticated control parameters and actions) from the elementary example described above which, however, provides a suitable environment for describing the invention.

As discussed above, it is known to monitor the $CO_2$ concentration in a conditioned space and, when the concentration of $CO_2$ reaches a predetermined level, to selectively admit outside air to lower the $CO_2$ level and accordingly raise the $O_2$ concentration to an acceptable level. Still referring to FIG. 1, it will be observed that provision has also been made to selectively admit outside air into the conditioned space. Further, this feature can be controlled in accordance with the $CO_2$ level measured in the conditioned space 2. A damper/heat exchanger block 14 includes conventional damper apparatus for selectively closing off or admitting outside air into the conditioned space 2 via conduit 17 (represented by the arrow 17A), damper/heat exchanger unit 14 and conduit 18 (represented by the arrow 18A). Similarly, provision has been made to selectively transfer air from the conditioned space 2 to the outdoors via conduit 15 (represented by arrow 15A), damper/heat exchanger unit 14 and conduit 16 (represented by arrow 16A).

It is well known in the art that heat can be transferred between the incoming outside air and the exhausted air from the conditioned space by coupling the respective conduits for conductive heat exchange. As an elementary example, a common wall 19 between the conduits 16, 17, if fabricated from a good heat conductor such as aluminum, steel or the like, serves as a simple heat exchanger for this purpose. Accordingly, if the conditioned space is being heated, some of the heat in the exhausted air can be used to raise the temperature of the incoming air; and if the conditioned space is being cooled, some of the reduced heat in the exhausted air can be used to lower the higher temperature of the incoming air. It will be understood that more elaborate conventional heat exchange elements can be included in damper/heat exchanger unit 14 to further increase the efficiency of the system.

Figure 2:
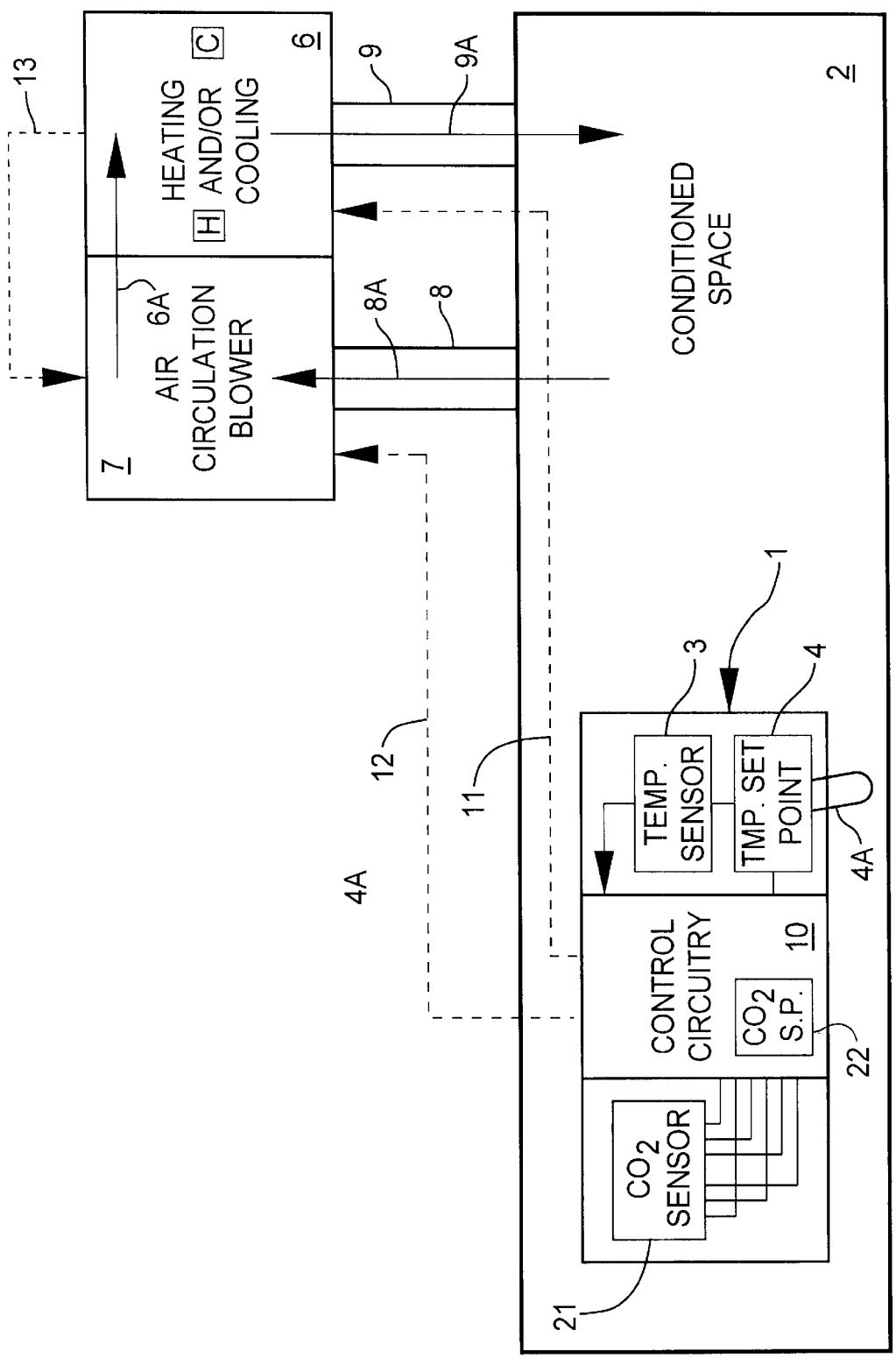
FIG. 2 is a high level block diagram illustrating a variant environment in which the present invention finds application.

Referring now to FIG. 2, in "leaky" buildings in which outside air routinely encroaches into the conditioned space (as, for example, by frequent opening of doors to the outside or by infiltration in a less completely sealed system), the $CO_2$ concentration in one building region, at which the integrated thermostat/$CO_2$ level detector unit 1 is situated, may become unacceptably high while remaining acceptable in other regions within the same heating/cooling system. In such an environment, it is not (or may not be) necessary to rely upon the deliberate exchange of conditioned air for outside air. Rather, the blower unit 7 may simply be turned on by the control circuitry 10, via signal line 12, to mix the air throughout the conditioned space until the $CO_2$ level at the integrated thermostat/$CO_2$ level detector unit 1 (as determined by the $CO_2$ sensor 21) drops below a predetermined level (as established by the $CO_2$ set point 22). It will be apparent that a plurality of integrated thermostat/$CO_2$ level detector units 1 can be distributed within such an environment with each such unit having the authority to actuate the blower unit 7 if the $CO_2$ concentration exceeds a predetermined level at a given unit.

As will be discussed further below, a system such as that shown in FIG. 1 which does provide for the selective admission of outside air can be operated to first only turn on the blower unit 7 when the sensed $CO_2$ concentration reaches a first concentration and to actuate the dampers in the dampers/heat exchangers unit 14 to admit outside air only if and when the sensed $CO_2$ concentration reaches a second, higher concentration, thereby limiting the necessity for taking in outside air with a consequent increase in energy efficiency.

Figure 3:
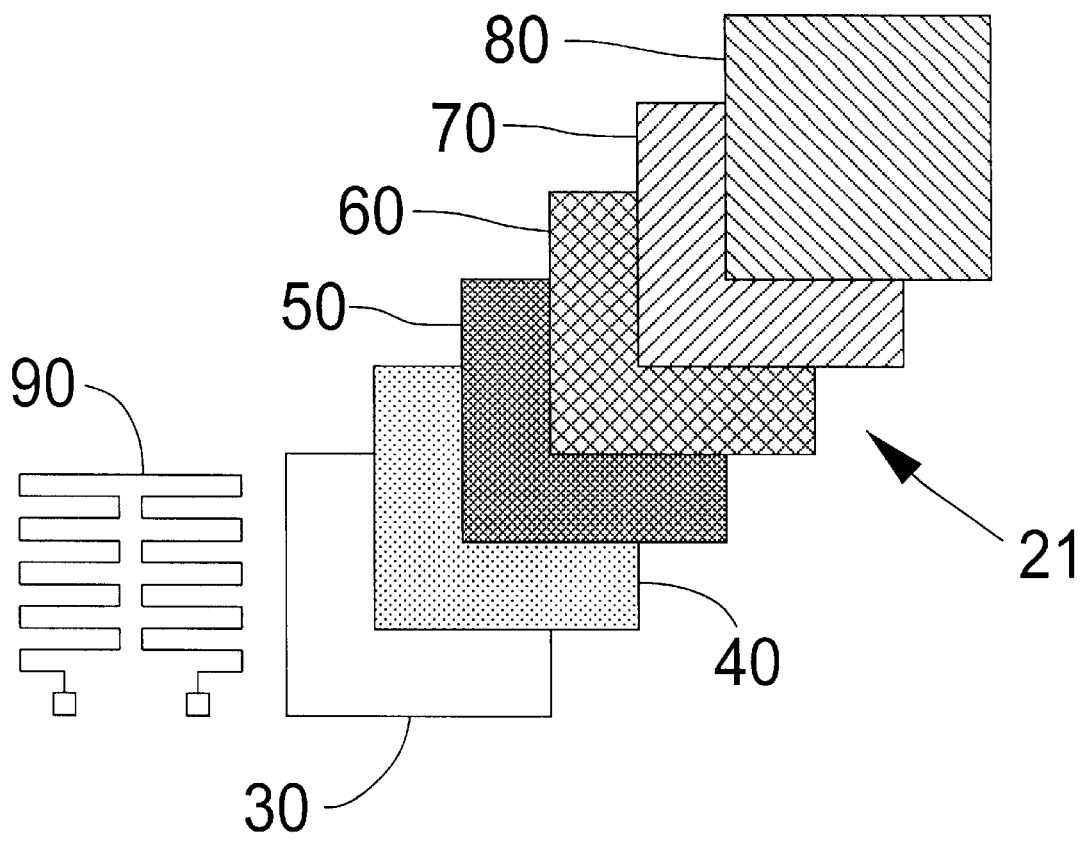
FIG. 3 is an exploded view of a $CO_2$ sensor employed in a presently preferred embodiment of the invention.
Figure 4:
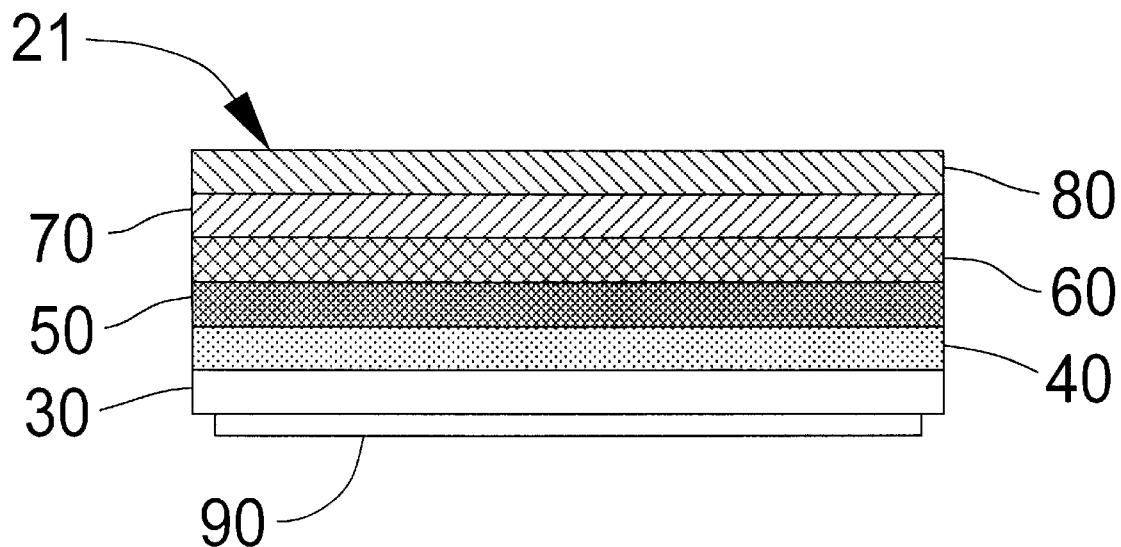
FIG. 4 is a side view of the $CO_2$ sensor shown in FIG. 3.

A $CO_2$ sensor 21 especially well-suited for use in the invention is shown in FIGS. 3 and 4. The $CO_2$ sensor 21, in a presently preferred embodiment, includes an aluminum oxide substrate 30 with an adjacent metal oxide (preferably NiO) ion reference layer 40. This reference layer 40 acts to provide a constant source of oxygen ions in the CO sensor 21 and thus minimizes drift in device response over time. Above the reference layer 40 is a lower catalytic electrode 50 (of, for example Pt), and above the lower catalytic electrode 50 is a solid electrolyte layer 60, which may, for example, be composed of a plurality of layers of tungsten stabilized bismuth oxide to promote $CO_2$ reactions. Also included is a buffer layer 70 (of, for example, yttrium stabilized zirconia) which helps prevent diffusion of unwanted ionic species into the first electrolyte layer 60. Above the first electrolyte layer 60 and the buffer layer 70 is an upper catalytic electrode 80, of, for example, Pt.

In addition to the above described layers, it is also useful to include a heating element layer 90 which can be disposed in thermal contact with the lower side of the aluminum oxide substrate 30. Stabilizing the $CO_2$ sensor 21 at a selected temperature within the range 30° C. to 300° C. enhances the accuracy of the $CO_2$ concentration measuring process.

Further details and aspects of exemplary $CO_2$ sensors (which may be employed as the $CO_2$ sensor 21) and their fabrication are described in U.S. Pat. No. 5,429,727, entitled Electrocatalytic Cermet Gas Detector/Sensor, Vogt et al, and in U.S. Pat. No. 5,772,863, entitled Electrocatalytic Cermet Sensor, Shoemaker et al, both of which are incorporated by reference herein.

Figure 5:
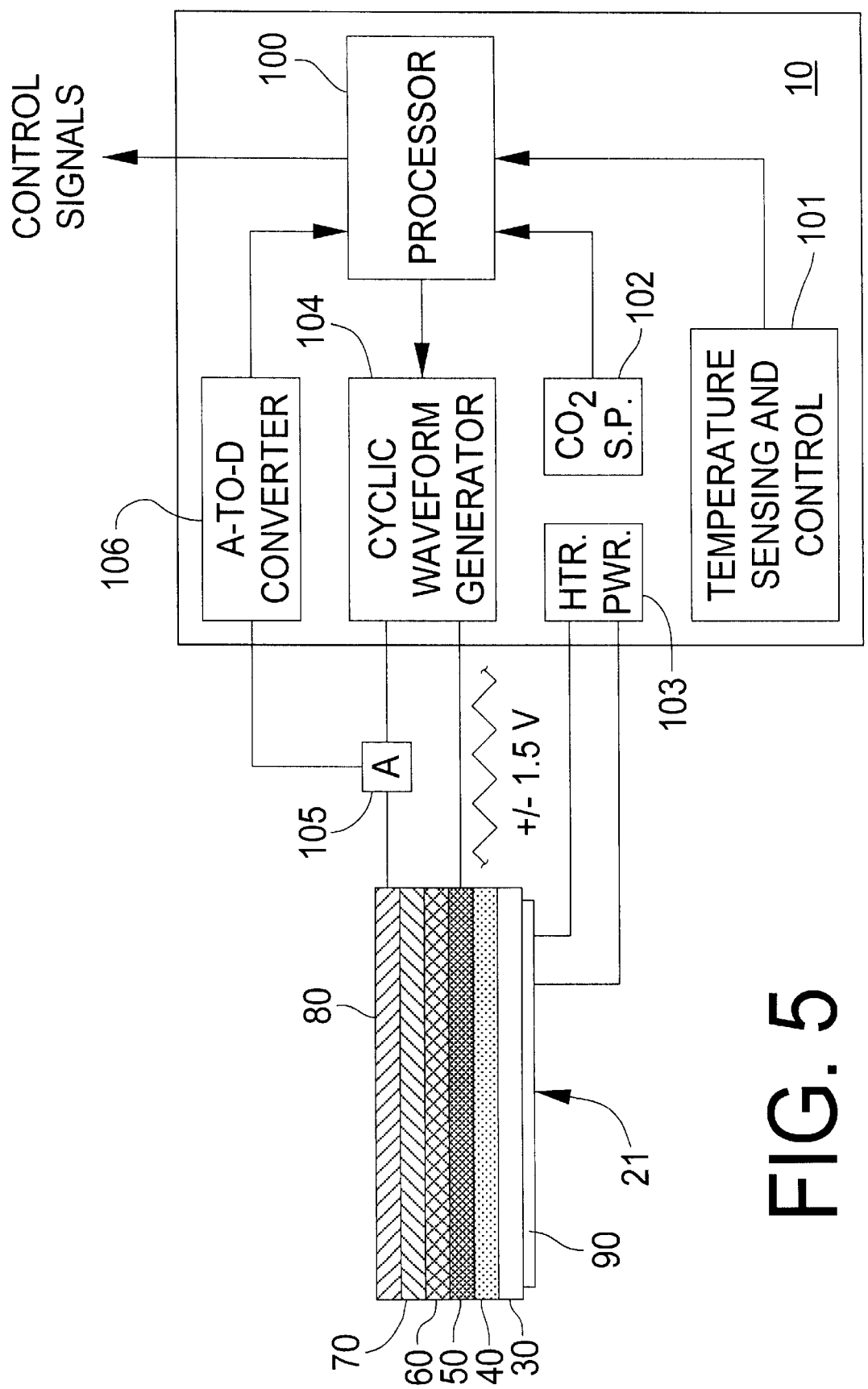
FIG. 5 is a more detailed partially block/partially schematic diagram of a presently preferred embodiment of the invention.

Attention is now directed to FIG. 5 which is a more detailed, partially schematic/partially block diagram illustrating the $CO_2$ sensor operatively connected into the $CO_2$ measuring apparatus components of the control circuitry 10. The operation of the control circuitry is supervised by a processor 100 which receives and conventionally processes temperature related information from conventional temperature sensing and control circuitry 101. In addition, the processor 100 directs a cyclic waveform generator 104 to apply a periodically varying voltage between the upper electrode 80 and the lower electrode 50. Exemplary peak-to-peak voltage excursion limits for the cyclic wave may be on the order of +/−1.5V, and one exemplary suitable waveform is triangular. As will be discussed further below, a $CO_2$ concentration measuring point may be considered as taken at a DC potential and phase which instantaneously exists between the upper 80 and lower 50 electrodes.

A current sensor 105 is disposed in-line with the voltage application circuitry to provide a constantly varying analog representation of the current passing between the electrodes 80, 50. An analog-to-digital converter 106 transforms an instantaneously sensed current (i.e., the instantaneous current sensed at a given application voltage and phase) to digital form for processing by the processor 100.

Figure 6:
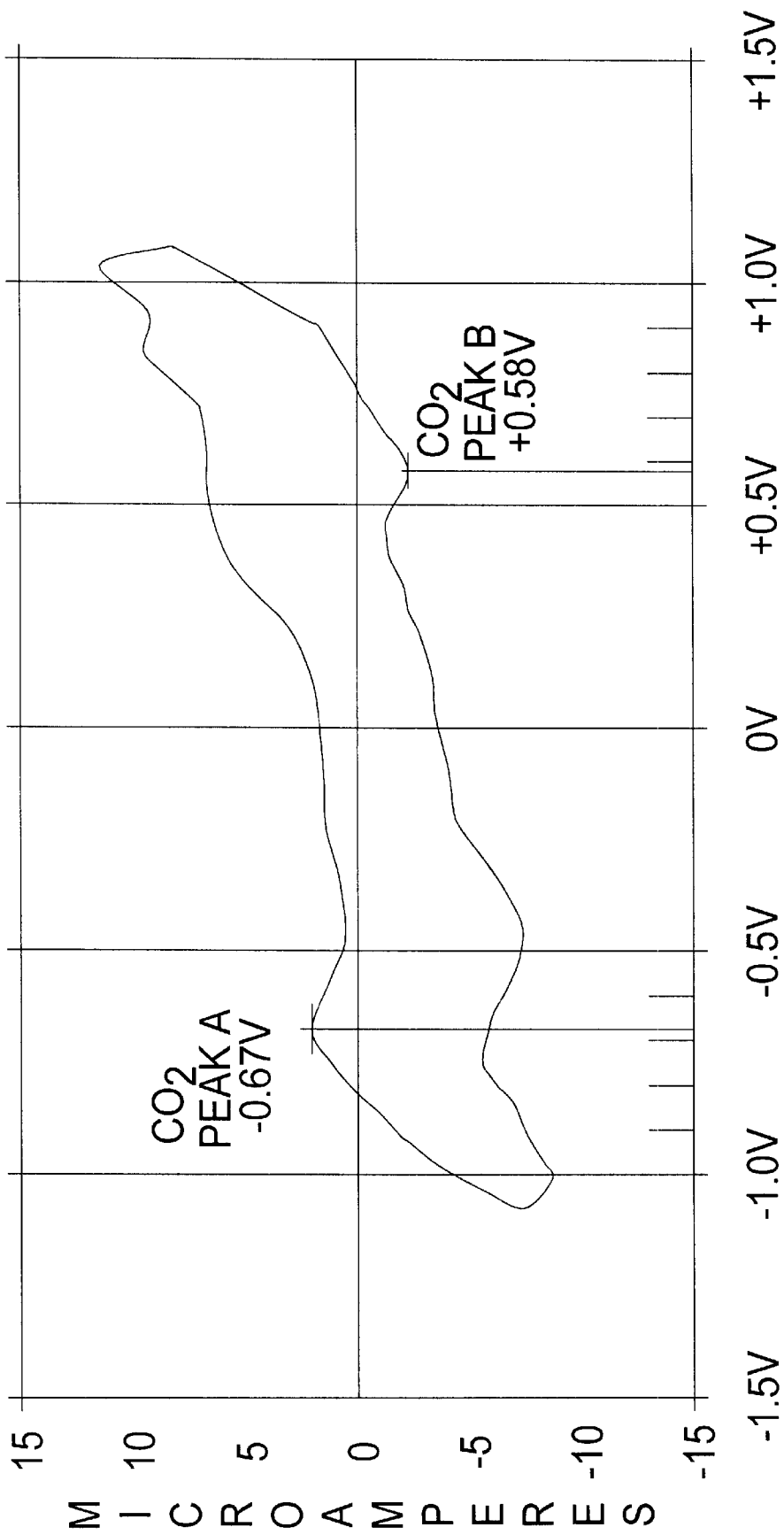
FIG. 6 shows an exemplary V/I curve showing the characteristics, including two $CO_2$ peaks, of a $CO_2$ sensor which may be employed in a presently preferred embodiment of the invention.

Referring also to FIG. 6, a characteristic V/I curve of the response of the $CO_2$ sensor 21 in a test environment of 0.01% $CO_2$ in nitrogen (representing air) is shown. Those skilled in the art will understand that a family of such curves can be readily generated under controlled test conditions for various $CO_2$ concentrations and stored as lookup tables in the processor 100 memory. (The applied voltage in this example is about +/−1.1V, and the waveform in this example is triangular.) Of fundamental importance is the appearance, in the exemplary characteristic curve, of two $CO_2$ current "peaks" appearing at instantaneous applied voltages −0.67V (Peak A) and +0.58V (Peak B). It will be understood that, in the family of curves to which that shown in FIG. 6 belongs, the $CO_2$ current "peaks" all are present at the same voltages with the actual current sensed being representative of the instantaneous $CO_2$ concentration at the $CO_2$ sensor 21. Those skilled in the precision measurement arts will understand that the subject measurement circuitry falls within the general category of a "potentiostat", but greatly miniaturized and particularly adapted to the described unique application integrated into a thermostat. It will be apparent that this is a fundamental departure in technology from that used in the above-identified co-pending application wherein the $CO_2$ sensor employed is a very specialized miniature primary cell which is subject to the above-noted drawbacks.

Accordingly, the processor controls the A-to-D converter 106 to repeatedly sample the current sensed by the current sensor 105 only at the instant(s) within a cycle that the applied wave voltage is at one or both the voltages at which the $CO_2$ current "peaks" will be present. Because the $CO_2$ current "peaks" appear at the same voltage points in all the curves in the family, the sensed current can be compared to the known values in the family of curves stored in the processor 100 which provides the actual $CO_2$ concentration information for comparison to the $CO_2$ set point(s) 102 in order to selectively issue various control signals to affect and limit the $CO_2$ concentration as previously described. Of course, various statistical techniques can be employed to increase the accuracy of the $CO_2$ concentration measurements. For example, many successive reading can be averaged to minimize the effects of the occasional anomalous reading.

If a heater is used (and such is preferable at the state-of-the-art of the $CO_2$ sensor 21 (although closely-related "room temperature" $CO_2$ sensors are contemplated), power may be supplied to the heater 90 from a heater power module 103 in the control circuitry 10. A conventional thermostat (not shown) may be employed to maintain the sensor temperature at a preferred temperature for a given set of conditions. However, "room temperature" $CO_2$ sensor 21 are in development, and their commercial use in the present application as soon as practical is contemplated.

Because the exemplary $CO_2$ detector and its associated circuitry is small and requires little power (notwithstanding the heating function), a very few integrated circuits, a hybrid circuit or even a single integrated circuit, can be fabricated and employed for effecting all the temperature control and $CO_2$ level control operations of the integrated thermostat/$CO_2$ level detector unit 1 which can therefore be provided as a single unit in a small housing.

Thus, while the principles of the invention have now been made clear in an illustrative embodiment, there will be immediately obvious to those skilled in the art many modifications of structure, arrangements, proportions, the elements, materials, and components, used in the practice of the invention which are particularly adapted for specific environments and operating requirements without departing from those principles.

What is claimed is:

1. A system for monitoring and modifying the quality and temperature of air within a conditioned space and including a blower unit, a temperature moderating unit and a control unit, said control unit comprising:
   A) a thermostat including temperature set point establishment means and temperature control means for selectively activating said temperature moderating unit when the temperature of the conditioned space deviates by a predetermined amount from the established temperature set point; and
   B) $CO_2$ concentration measuring and control apparatus for the conditioned space, said $CO_2$ concentration measuring and control apparatus comprising:
      1) a $CO_2$ sensor comprising:
         a) a reference electrode source of oxygen anions;
         b) a lower electrical reference electrode coupled to said reference electrode source of anions;
         c) a solid electrolyte coupled to said lower reference electrode;
         d) a buffer layer; and
         e) an upper electrode coupled to said buffer layer;
      2) $CO_2$ concentration measuring apparatus in which:
         a) an electrical voltage is applied between said lower electrical reference electrode and said upper electrical electrode, said electrical voltage having a cyclic waveform and instantaneous values between a predetermined negative voltage and a predetermined positive voltage; and
         b) the current through said electrolyte measured, at a predetermined voltage intermediate said predetermined negative voltage and said predetermined positive voltage, is representative of the $CO_2$ concentration; and
      3) $CO_2$ concentration modifying apparatus responsive to the measurement of at least a first predetermined $CO_2$ concentration for turning on said blower unit.

2. The system of claim 1 in which said $CO_2$ sensor is emplaced on a substrate which also carries a heater serving to maintain said $CO_2$ sensor at a predetermined temperature.

3. The system of claim 2 in which said predetermined temperature falls within the range of 30° C. and 300° C.

4. A system for monitoring and modifying the quality and temperature of air within a conditioned space and including a damper unit for selectively admitting outside air into the conditioned space, a temperature moderating unit and a control unit, said control unit comprising:
   A) a thermostat including temperature set point establishment means and temperature control means for selectively activating said temperature moderating unit when the temperature of the conditioned space deviates by a predetermined amount from the established temperature set point; and
   B) $CO_2$ concentration measuring and control apparatus for the conditioned space, said $CO_2$ concentration measuring and control apparatus comprising:
      1) a $CO_2$ sensor comprising:
         a) a reference electrode source of oxygen anions;
         b) a lower electrical reference electrode coupled to said reference electrode source of anions;
         c) a solid electrolyte coupled to said lower reference electrode;
         d) a buffer layer; and
         e) an upper electrode coupled to said buffer layer;
      2) $CO_2$ concentration measuring apparatus in which:
         a) an electrical voltage is applied between said lower electrical reference electrode and said upper electrical electrode, said electrical voltage having a cyclic waveform and instantaneous values between a predetermined negative voltage and a predetermined positive voltage; and
         b) the current through said electrolyte measured, at a predetermined voltage intermediate said predetermined negative voltage and said predetermined positive voltage, is representative of the $CO_2$ concentration; and
      3) $CO_2$ concentration modifying apparatus responsive to the measurement of at least a first predetermined $CO_2$ concentration for actuating said damper unit to admit outside air into the conditioned space.

5. The system of claim 4 in which said $CO_2$ sensor is emplaced on a substrate which also carries a heater serving to maintain said $CO_2$ sensor at a predetermined temperature.

6. The system of claim 5 in which said predetermined temperature falls within the range of 30° C. and 300° C.

7. A system for monitoring and modifying the quality and temperature of air within a conditioned space and including a blower unit, a damper unit for selectively admitting outside air into the conditioned space, a temperature moderating unit and a control unit, said control unit comprising:
   A) a thermostat including temperature set point establishment means and temperature control means for selectively activating said temperature moderating unit when the temperature of the conditioned space deviates by a predetermined amount from the established temperature set point; and
   B) $CO_2$ concentration measuring and control apparatus for the conditioned space, said $CO_2$ concentration measuring and control apparatus comprising:
      1) a $CO_2$ sensor comprising:
         a) a reference electrode source of oxygen anions;
         b) a lower electrical reference electrode coupled to said reference electrode source of anions;
         c) a solid electrolyte coupled to said lower reference electrode;
         d) a buffer layer; and
         e) an upper electrode coupled to said buffer layer;
      2) $CO_2$ concentration measuring apparatus in which:
         a) an electrical voltage is applied between said lower electrical reference electrode and said upper electrical electrode, said electrical voltage being a cyclic waveform and instantaneous values between a predetermined negative voltage and a predetermined positive voltage; and b) the current through said electrolyte, measured at a predetermined voltage intermediate said predetermined negative voltage and said predetermined positive voltage, is representative of the $CO_2$ concentration; and 3) $CO_2$ concentration modifying apparatus:

a) being responsive to the measurement of at least a first predetermined $CO_2$ concentration for turning on said blower unit; and b) being responsive to the measurement of at least a second predetermined $CO_2$ concentration, higher than said first predetermined $CO_2$ concentration, for actuating said damper unit to admit outside air into the conditioned space.

8. The system of claim 7 in which said $CO_2$ sensor is emplaced on a substrate which also carries a heater serving to maintain said $CO_2$ sensor at a predetermined temperature.

9. The system of claim 8 in which said predetermined temperature falls within the range of 30° C. and 300° C.

* * * * *